United States Patent
Klee

(10) Patent No.: US 8,845,794 B2
(45) Date of Patent: Sep. 30, 2014

(54) NON-SEIZING TAPERS FOR USE IN PURGED CONNECTIONS OF CAPILLARY TUBING USED IN GAS CHROMATOGRAPHY

(71) Applicant: Matthew Spangler Klee, Wilmington, DE (US)

(72) Inventor: Matthew Spangler Klee, Wilmington, DE (US)

( * ) Notice: Subject to any disclaimer, the term of this patent is extended or adjusted under 35 U.S.C. 154(b) by 0 days.

(21) Appl. No.: 14/170,719

(22) Filed: Feb. 3, 2014

(65) Prior Publication Data

US 2014/0150660 A1    Jun. 5, 2014

Related U.S. Application Data

(63) Continuation of application No. 14/106,775, filed on Dec. 15, 2013, now abandoned.

(51) Int. Cl.
*B01D 53/02* (2006.01)
*G01N 30/12* (2006.01)
*G01N 30/16* (2006.01)
*G01N 30/10* (2006.01)
*G01N 30/60* (2006.01)
*G01N 30/02* (2006.01)

(52) U.S. Cl.
CPC ............ *G01N 30/60* (2013.01); *G01N 30/6026* (2013.01); *G01N 30/12* (2013.01); *G01N 30/6004* (2013.01); *B01D 53/02* (2013.01); *G01N 30/6078* (2013.01); *G01N 2030/6008* (2013.01); *G01N 2030/025* (2013.01); *G01N 30/16* (2013.01); *G01N 30/10* (2013.01); *B01D 53/025* (2013.01); *G01N 30/6034* (2013.01); *G01N 2030/167* (2013.01); *G01N 30/6039* (2013.01)
USPC ..... 96/106; 96/101; 96/105; 95/89; 73/23.35; 73/23.39; 73/23.42

(58) Field of Classification Search
CPC ...... B01D 53/02; B01D 53/025; G01N 30/10; G01N 30/12; G01N 30/16; G01N 30/60; G01N 30/6004; G01N 30/6034; G01N 30/6039; G01N 30/6078; G01N 2030/6008; G01N 2030/167
USPC .......... 96/101, 105, 106; 95/82, 89; 73/23.35, 73/23.39, 23.41, 23.42
See application file for complete search history.

(56) References Cited

U.S. PATENT DOCUMENTS

| 4,035,168 A | 7/1977 | Jennings | |
| 4,440,550 A * | 4/1984 | Jenkins et al. | 95/89 |

(Continued)

OTHER PUBLICATIONS

Matthew S. Klee, GC Solutions #36: Inlet Liners—Part 1, Eclipse Business Media Ltd, www.sepscience.com, date unknown.*

(Continued)

*Primary Examiner* — Robert Clemente

(57) ABSTRACT

A non-seizing taper used for purged capillary tubing connections in gas chromatography that stops capillary tubing at a predictable position within the taper during installation and maintains space for gas to flow past the capillary tubing. The disclosed taper is an improved component of commonly used purged devices such as inlet liners and purged unions. The arresting aspect of the taper simplifies the process of capillary tubing installation while ensuring that the tubing will reproducibly be positioned in the taper. One or more features of the taper prevent tubing from seizing within the taper so that the devices can be reused and ensure that there is open space for a portion of gas to flow around and past the tubing. The angle of the taper, the dimensions of the taper, and the nature of the features within the taper can be adjusted to meet specific performance, usability and/or manufacturability requirements.

15 Claims, 9 Drawing Sheets

(56) References Cited

U.S. PATENT DOCUMENTS

| | | | |
|---|---|---|---|
| 5,215,340 | A | 6/1993 | Ledford, Jr. |
| 5,288,113 | A | 2/1994 | Silvis et al. |
| 6,203,597 | B1 | 3/2001 | Sasano et al. |
| 6,494,939 | B1 * | 12/2002 | Tipler .............................. 96/105 |
| 6,709,027 | B2 | 3/2004 | Rittenhouse |
| 6,969,095 | B2 * | 11/2005 | Rittenhouse .................. 285/332 |
| 7,867,325 | B2 * | 1/2011 | Jones et al. ..................... 96/105 |
| 8,506,688 | B2 * | 8/2013 | De Zeeuw et al. .............. 96/106 |
| 2007/0000828 | A1 | 1/2007 | Norman et al. |

OTHER PUBLICATIONS

Matthew S. Klee, GC Solutions #36: Inlet Liners—Part 1, Eclipse Business Media Ltd, www.sepscience.com Date Unknown.

GC and GC/MS Your Essential Resource for Columns and Supplies, Publication 5991-1058EN, Agilent Technologies, Inc., 2012, www.agilent.com.

"Inlet Liner Geometry and the Impact on GC Sample Analysis", SGE publication TA-0145-A, SGE Analytical Science Pty Ltd, Melbourne, Australia, www.sge.com.

"Capillary GC Inlet Liner Selection Guide", Supelco Bulletin 899A, 1997, Supelco, Supelco Park, Bellefonte, PA, www.sigmaaldrich.com.

Scott Grossman, Corby Hilliard, Jack Cochran, Rick Morehead, "Form & Function II: Understanding the Complex World of GC Inlet Liners, An analysis of liner choice on splitless & direct injection techniques", Restek Corporation, 110 Benner Circle, Bellefonte PA 16823, www.restek .com, 2011.

Matthew S. Klee, "GC Solutions #6: Hot Split Injections, Part 2—Sources of Discrimination", Eclipse Business Media Ltd, Cheshire CW5 6PQ, United Kingdom, www.sepscience.com.

Matthew S. Klee, GC Solutions #22: Inlet Activity, Eclipse Business Media Ltd, Cheshire CW5 6PQ, United Kingdom, www.sepscience.com.

Matthew S. Klee, GC Solutions #34: Split Sample Introduction—Part 2: Measuring Flows, Liner, ChoiceEclipse Business Media Ltd, Cheshire CW5 6PQ, United Kingdom, www.sepscience.com.

Flexible Fused Silica Capillary Tubing brochure, 2011, Polymicro, 18019 N. 25th Avenue • Phoenix, AZ 85023-1200, www.polymicro.com.

* cited by examiner

NON-SEIZING TAPERS FOR USE IN PURGED CONNECTIONS OF CAPILLARY TUBING USED IN GAS CHROMATOGRAPHY

TECHNICAL FIELD

This invention relates generally to the field of instrumentation for chemical analysis but has specific application to purged connections of capillary tubing used in conjunction with gas chromatographs.

CLASS 96/106; 96/101

Note: This is a continuation of prior-filed pending non-provisional application Ser. No. 14/106755 filed Dec. 15, 2013.

BACKGROUND OF THE INVENTION

Gas chromatographs are used for chemical analysis. Chromatographic techniques in general are used and for chemical analysis of mixtures because they can partially or completely separate mixtures into individual components, thereby providing unique information about sample composition. Gas chromatography is often chosen over other potential chromatographic techniques because of its speed of analysis, unique detectors, lower cost per sample and simplicity of use.

Determining what is in a sample is called "qualitative analysis". Determining how much of given substance is in a sample is termed "quantitative analysis". Quantitative analysis requires qualitative analysis; one must first confirm presence of a component prior to determining how much is there. However qualitative analysis does not require quantitative analysis. Gas chromatography can provide both quantitative and qualitative of information. Because of the unique performance characteristics of GC detectors, the range of quantification can span up to seven orders of magnitude; much higher than with other chromatographic techniques.

A block diagram of a gas chromatograph (GC) is illustrated in FIG. 1. It consists of a source of flowing gaseous mobile phase, a means of introducing sample into the stream of mobile phase (sample inlet), a capillary column containing a stationary phase through which mobile phase and sample flow, a detector at the end of the column to detect eluting sample solutes, a means recording the detector signal as a function of time, and a means of controlling all of the above.

In gas chromatography, helium, hydrogen, and nitrogen are preferred as mobile phase gases because of their high diffusivity, low viscosity and relatively low cost. The mobile phase, for example helium, is continually flushed through the column. The column is placed in an oven that is maintained at an isothermal temperature or subjected to a specific temperature program. By adjusting the temperature or temperature program, the quality of separation for a given sample type can be optimized. Typical temperatures used in gas chromatography fall in the range from 30° C. to 350° C. although some commercial instruments can be cryogenically cooled to as low as allowed by the cryogen being used and heated to over 400° C. for specific applications.

To perform a GC analysis, a sample mixture is introduced into the chromatograph and enters the beginning of the chromatographic column. It is driven toward the end of the column by the gaseous mobile phase. Sample components (also called solutes or analytes) have the potential as they travel through the column under the force of the mobile phase to separate from each other through selective interactions with the stationary phase contained in the column. Upon emerging from the end of the column, a detector with the appropriate response characteristics provides a change in signal that indicates the time of elution (qualitative information) and, by the magnitude of the response, the amount of the component present (quantitative information).

One popular type of column used in gas chromatography is in the form of an open tubular capillary column. The preferred type of tubing used for capillary columns varies depending on the sample characteristics and the analytical requirements. Due to its wide range of applicability and favorable characteristics, the most common capillary tubing material used for gas chromatography is composed of fused silica coated on the outside with a protective layer, usually polyimide, to provide flexibility and to prevent breakage. Capillary tubing is also used in several others forms of chromatography in addition to gas chromatography such as capillary liquid chromatography and capillary electrophoresis. Depending on the type of sample and analytical needs, capillary columns used in gas chromatography will have different forms of stationary phase, such as those listed below.

1. Stationary phase particles immobilized as layers on the inner surface of fused silica capillaries in a manner that maintains the general openness of the internal diameter of the capillary. This style of column is called a Porous Layer Open Tubular (PLOT) column.
2. A non-volatile liquid stationary phase is coated and sometimes immobilized on the inner surface of the fused silica capillary. This style of column is called a Wall Coated Open Tubular (WCOT) column.

Table 1 compares the typical dimensions of fused silica capillary tubing and stationary phases used in capillary column gas chromatography.

TABLE 1

Typical capillary tubing dimensions and stationary phase types used in gas chromatography.

| Range of Column Lengths | Typical Range of Inner Diameters | Typical Range of Outer Diameters | Thickness Range and Type of Stationary Phase |
|---|---|---|---|
| 5-100 m | 0.32-0.53 mm | 0.4-0.8 mm | 20-50 μm layers of solid adsorbents (PLOT columns) |
|  | 0.10-0.53 mm | 0.25-1.0 mm | 0.1-5 μm of non-volatile liquids (WCOT columns) |

The same capillary tubing that is used to make chromatographic columns is sometimes also used without stationary phase. For example, it has been shown that by using a short length of uncoated tubing between a chromatographic inlet and a coated column, some of the problems encountered with recondensed solvent, typical of splitless mode of sample introduction, can be minimized. In further examples, uncoated tubing is used with chromatographic column effluent splitters when connecting to multiple detectors and/or to provide restriction necessary when connecting to mass spectrometers. Problems found with connections of uncoated capillary tubing to inlets and other purged connections are the same whether or not the tubing contains stationary phase, so for the purposes of describing the current disclosure, the terms capillary column and capillary tubing should be considered to be interchangeable.

When a capillary column is mounted in a gas chromatograph, the inlet end of the column is attached to an inlet. Inlets are sometimes also called injectors, but since the term injector is also used for the automated devices that inject liquid samples into inlets, the term inlet will be used hereafter when referring to the interface to which a capillary column is attached and through which samples are introduced and transferred to the column.

In gas chromatography, the inlet is typically housed in the gas chromatograph in a vertical configuration exterior to but extending into the column oven; the inlet base protruding into the column oven. Capillary columns, generally housed in the column oven, are typically reversibly sealed to the base of the inlet using a deformable tapered ferrule and compression nut. Not only do inlets provide the means for introduction of samples and subsequent transfer to chromatographic columns, they also perform other useful functions including evaporation and/or concentration of samples, splitting the vaporized sample to reduce the amount of sample reaching the column, narrowing of the initial time width of the sample reaching the column, and protection of the column from nonvolatile sample components.

There are several types of gas chromatography inlets. The most commonly used with capillary columns is called a split/splitless inlet. Split/splitless inlets are available in constant temperature (isothermal) and in programmed-temperature designs. The split/splitless terminology refers to the two dominant modes of sampling with these inlets: split mode and splitless mode.

The basic flow design of a split/splitless inlet is shown in FIG. 2. There are other designs that differ in some design choices, but all designs provide the capability of splitting of flows that travel through the inlet into several paths. A total flow of carrier gas is fed to the inlet. The inlet provides three potential flow paths between which the total flow can be split. A septum purge flow 204 is typically a low flow (e.g., 3 mL/min) and is directed across the top of the inlet to prevent contaminants that outgas from the polymeric septum at the top of the inlet from entering the liner and eventually reaching the column. The remaining flow 203, composed of the combination of column and split flows, travels down the inlet within an inlet liner. Capillary column flow 206 exits the bottom of the inlet and enters the capillary column and is typically 0.5 to 5 mL/min, driven by a specific predetermined inlet pressure. Split vent flow 205 (also called purge flow when performing sample introduction in splitless mode) is usually large relative to column and septum purge flows. It passes around and by the head of the column, travels under the base of the liner in the space between the liner and an inlet baseplate, up the inlet within the space between the liner and the inlet weldment, and then out a split vent line 211. A backpressure regulator 210 in the split vent line restricts the split flow to provide the setpoint pressure necessary to drive carrier gas flow through the capillary column at the desired rate. A split vent trap 208 protects the backpressure regulator by trapping vented sample components before they can reach the backpressure regulator. Inlet pressure is measured by a pressure sensor 112 that is in common with the septum purge line, where it has minimal exposure to sample vapors.

In split mode, the split vent valve 209 is open during the full period of sample introduction and sample transfer to the column. The objective is to reduce the mass of sample reaching the column so that it does not overload the capacity of the stationary phase and thereby degrade chromatographic performance. The splitting process also narrows the width of initial sample plug reaching the column, which is also important for obtain optimal chromatographic performance.

In splitless mode, the split vent valve 209 is closed for a user-defined period of time starting from just before sample is injected into the inlet. The objective of using splitless mode is to transfer all or a majority of the sample to the column. The total flow entering the inlet during sample introduction and sample transfer in splitless mode, then, is the sum of just the septum purge and column flows. Flow 203 down the inlet liner is equal to the column flow 206; therefore sample transfer to the column is a much slower process than in split mode. Since most of the sample is transferred to the column in splitless mode, the solvent peak (usually the major sample component) is very large and its peak width quite wide with an exponential tail that can extend significantly into the time period of the analysis, complicating analysis of minor sample components. To decrease or eliminate the solvent tail, the split/purge valve is opened at the user-specific time after sample introduction (typically 0.5 to 2 min after injection). The purge flow quickly sweeps remaining solvent vapors out of the inlet and remains on for the duration of the run thereafter to minimize transfer of low volatility contaminants from the inlet to the column.

With both split and splitless modes of sample introduction, a common goal is that the sample that reaches the column is the same composition and relative concentration as that in the original sample. This is called representative sampling. In all cases, even when there is not representative sampling, it is important that the resulting sample transfer process is reproducible from run to run and over time. Many of the developments in gas chromatographs over the years have been aimed at achieving more representative and reproducible sampling for the ever increasing range of applications to which gas chromatography is being applied.

It is very difficult to achieve truly representative sampling in gas chromatography because the sample must change from a condensed state to a gaseous state and then must undergo the physical process of transferring down and out of the inlet into the column. There are multiple variables that influence the actual sample composition that reaches the column. Some of the variables that influence sample composition reaching the column are:

Inlet temperature
Inlet pressure
Carrier gas flow rate
Carrier gas control (response time, sensitivity, and range)
Chemical and physical nature of the sample components
Volume of sample introduced
Sample solvent type
Manner of sample introduction (manual or automated, slow or fast, syringe type, etc.)
Inlet liner shape, features and internal volume
Presence or absence of glass wool in the liner
Presence of and dimensions of a reduced bore at the base of the liner
Adsorptive and catalytic activity of the inlet surfaces
Position of the column end in the inlet liner
Resistance of flow around the base of the liner
Tightness of the liner in the inlet weldment The changes in sample composition caused by non-ideal sample introduction and transfer processes in gas chromatography can manifest as an increase or decrease in the relative amounts of components as a function of their volatilities, resulting in non-representative sampling. This is commonly categorized as discrimination. Partial or complete losses of specific components can also occur due to degradation (decomposition or other chemical or physical changes in the sample component) or adsorption on active inlet surfaces. When a sample component decomposes, the original component is chemically converted to one or more new components. When a component is irreversibly adsorbed on a surface, either partially or completely, its apparent quantitative amount will be reduced relative to that in the original sample.

The magnitude of sample losses observed with a given sample, method, instrument, and set of setpoints is highly dependent on both the design of the inlet liner and the variability in column positioning at the base of the liner. The current art includes many different styles of liners, each with design attributes that are favorable for some analyses but unfavorable for others. The opinions of those skilled in the art of the optimal liner design features has changed over the years. This is partially due to expanded use of capillary gas chromatography into new areas as well as changes in the design and performance characteristics of commercial gas chromatographs.

Repeatable sampling in gas chromatography is highly dependent on what happens during sample introduction into and transfer from the inlet to the column. The goal of reaching optimal sampling when using gas chromatography split/splitless inlets is constrained to a large degree by the design of the liner that is housed within the inlet weldment and by the variability in positioning of the column entrance within the inlet's and liner's bases.

The current art includes many different liner designs, several patented, that are aimed at improving the quality of sample transfer. An inlet liner is a narrow tube, typically composed of borosilicate glass that fits inside a specific inlet weldment, literally providing a liner for the inlet. Liners are typically deactivated with a coating or chemical derivatization process that reduces liner activity toward polar and/or labile sample components. It is a common practice to replace inlet liners on a regular basis as they become contaminated or when the deactivation layer depletes and the liner becomes too active. When liners are replaced, the capillary columns in use are also typically detached from the inlet base, trimmed and then reinstalled along with the new liner. There are several variables relating to liner and column positioning that can result in a change in analytical performance whenever liners are changed and columns reinstalled.

Liner internal volumes must be large enough to contain the volume of evaporated sample, and therefore liner internal diameters are typically many times the internal diameter of the capillary column that are positioned at their bases. The outer diameters of liners are constrained by the size of the inlet weldment into which they are inserted.

It is well known in the art that liners with straight internal diameters can suffer from issues of sample discrimination, decomposition, and peak broadening. As illustrated in FIG. 3, the under-sampling of high molecular weight, less volatile sample components occurs with straight liners because the larger molecules tend to migrate preferentially 307 down the wall of the liner 302 and do not enter the column in proportion to their concentration in the sample. In addition, liners with wide bases leave a large area of the inlet weldment base 305, often called the baseplate, exposed. The baseplate is typically composed at least partially of metal and typically has higher activity toward labile sample components than glass liners. An additional deficiency of straight liners is that the concentric positioning of the column tip within its base is irreproducible, even with the same person doing the installation. This decreases consistency in results before and after column changes, or column removal, trimming, and reinstallation as is common during routine maintenance.

A key design element in the current art that helps to improve performance compared to straight liners and liners with wide internal diameters at their bases is the incorporation of a straight bore of smaller internal diameter at the bottom of the liner, as illustrated in FIGS. 4 and 5. The inner bore of the liner tapers to a bore of reduced diameter 411 at the liner base. The diameter of the smaller bore approaches that of the outer diameters of the capillary columns 403 that could be positioned therein. By tapering to a smaller internal diameter, less volatile components that preferentially migrate near the inner wall of the liner are brought into closer proximity to the column entrance 408 and are thereby more representatively sampled. In addition, narrowing of internal diameter at the liner base has other advantages including reduced exposure of sample vapors and/or unevaporated sample droplets to the metal baseplate and/or any contaminants that might have accumulated at the bottom of the inlet weldment. This improves recovery of active and labile sample components.

For optimal benefit from a narrowed internal diameter at the liner base, column ends should be positioned centrally within the bore of the liner taper. Capillary tubing inserted too far up protrudes into the larger internal diameter of the liner and does not benefit from the tapered internal diameter. Columns not inserted far enough expose more sample to the inlet baseplate.

The aspect ratio of the taper bore to the outer diameter of the column and the exact position of the column end within the taper bore can also influence sampling performance. Even with an optimized aspect ratio, different insertion distances of the column end inside the bore will change the pneumatic resistance and dynamics of gas flow around the column entrance. Reproducibly positioning of the end of the column inside the narrowed bore of the liner is somewhat difficult in the current art, especially with different operators, instrument models and locations.

There is little or no published information that teaches the optimum aspect ratio of the taper diameter to that of the outer or inner diameters of the capillary column. It is obvious that at the one extreme is a straight liner bore with no reduction in diameter at the base, with which one would see no benefit. At the other extreme would be a diameter so small that the column either could not be inserted therein, or would be so tight that split/purge flow around the column would be restricted, or that the column would seize in the bore. It is reasonable for those skilled in the art to expect that having a different aspect ratio between the column diameter and the liner bore into which it is inserted could lead to a difference in analytical performance. In addition, differences in the position of the column end within a given bore could lead to different analytical performance.

Since both the split and splitless modes of inlet operation require that there be a flow of split or purge gas around and by the head of the column during all or part of the sample introduction and transfer process, it is important that the difference between the inner diameter of the reduced bore and the outer diameter of the column inserted therein not be so small as to restrict purge flow. Such a restriction could exaggerate the negative consequences of several variables involved with sample evaporation and transfer to the column as well as complicate pneumatic control.

It is reasonable for those skilled in the art to expect that the optimal aspect ratio of the liner taper internal diameter to the capillary column outer diameter is different for different applications. In addition, the optimal aspect ratio of space for gas flow around the column to the column's internal diameter might be smaller for splitless injection mode than for split injection mode. Differences in sample and solvent types and gas chromatographic method setpoints including temperature carrier gas type, pressure, flow rate, and injection volume, amongst other things can also impact optimal aspect ratio. Due to the high number of variables, in order to be generally applicable across a range of column diameters and applications and minimize manufacturing costs, manufacturers of inlet liners currently provide designs with generic dimensions that are designed to accommodate the largest column diameters and which therefore are suboptimal for many specific applications, especially those that use smaller diameter columns.

There exists in the art an inlet liner feature that is designed to capture and seal the end of fused silica capillary columns within it. This design incorporates a continuously narrowing, conical taper at the bottom of the liner as illustrated in FIG. 5. Columns 504 are inserted into the taper and pressed into the taper tightly such that the polyimide outer coating of the capillary forms a seal 502 against the surface of the taper.

This press-fit style of liner ensures that all sample vapors introduced into the liner flow into the column and has been shown to significantly reduce discrimination and improve recovery of active sample components. These liners must incorporate a side hole 503 in the larger internal diameter section of the liner to accommodate the split/purge flow required to improve solvent peak shapes and allow proper pneumatic control of the inlet. Two significant deficiencies of this style liner are that (1) they are designed for only splitless injections, and (2) typically can only be used for a single column installation. When replacing the liner or when removing the column, the seal between the end of the column and the conical taper has to be broken. Remnants (shards of fused silica and/or flakes of polyimide) inevitably remain adhered to the connection point, preventing the formation of subsequent pneumatic seals and/or increasing liner activity.

Each inlet liner design will have a specific optimal column position. It is the responsibility of the GC operator to know the target position and to ensure that the final column positioning is correct. Each operator adopts his own technique to accomplish this task but each has limitations.

Capillary column installation is time consuming, often cumbersome to perform and is prone to variability among and between operators. All current art for installing capillary columns into gas chromatograph inlets suffer from the stack up of variability in design choices and operator use. Column positioning errors can degrade method performance in several ways including but not limited to increased discrimination, increased loss of labile components, decreased chromatographic efficiency due to broadening or tailing of initial peak widths, leaks, and/or infiltration of air.

The following process of installing a capillary gas chromatographic column is commonly employed. A nut and ferrule are slipped over the end of a capillary column. Optionally, an inlet septum is inserted onto the column prior to adding the nut and ferrule. Following insertion through the ferrule, the operator cleaves a small length of tubing from the end of the column to be sure the operative column end is open and free of small particles or ferrule shavings which would obstruct the flow of mobile phase during chromatographic separation and cause additional deleterious effects. The operator then either marks the column at the back side of the nut after measuring the specified distance, pre-tightening the ferrule onto the column at the target position using a pre-swaging tool to fix into position, or slides the optional inlet septum up to hold the nut at the prescribed distance from the column end. Once at the specified length the column-ferrule-nut combination is inserted into the base of the inlet and the nut is tightened to form a pneumatic seal. During the sealing process, the vertical column position can shift as can the position of the column tip along the radial axis of the liner.

There are alternative column installation and affixing approaches in the current art that aim to simplify the process of column installation and increase repeatability of installing columns; however these approaches have a combination of deficiencies that limit their adoption and those skilled in the art have generally not found them to be improvements over the previously stated process. The limitations include prohibitive cost, complexity, necessity for stocking of non-standard parts, and inability to achieve the intended performance or benefits.

Not only is there potential variability in positioning the column due to operator variability and random errors, the position of the liner in the inlet weldment can also vary. Irreproducibility in positioning of the liner in the inlet weldment in turn leads to irreproducibility in positioning of the column end in the optimal position within the liner base. When liners are inserted into weldments, they can end up in different positions relative to the base of the inlet; flush with the weldment base or some distance off the base. Having the liner tight against the baseplate can lead to excessive resistance to flow of gas around the base to the split/purge vent, causing pressure control issues and decreasing sample introduction and transport performance. For this reason, some liner designs incorporate offset bumps or cutouts on their bases to ensure that even when pushed to the bottom of the inlet, there remains a low resistance pathway for around the base. In the current art, repeatable positioning of the column end within the base of the liner requires knowledge of the concepts involved, minimal impact of random variables, and accurate operator proficiency in positioning of column during installation.

Most gas chromatography inlet liners are made of borosilicate glass. The manufacturing process of glass liners, other than straight liners, typically includes a combination of traditional glass blowing techniques to form the desired features such as fusing dissimilar pieces together, pulling tapers, forming indentations or other features, or sealing of parts within the bore of the liner. In addition, production of some glass liners can include manual mechanical grinding, cutting, and/or drilling processes. Although the art of reproducibly forming sub-millimeter features of relatively high tolerance in glass using a mandrel is known, this technique is not required for manufacturing of current inlet liners.

In addition to liners for gas chromatograph inlets that allow purge gas flow around the column entrance, there are in the art purged connections used for coupling of capillary columns. Use of purged unions in capillary gas chromatography is becoming increasing popular for several applications including capillary column back-flushing, effluent splitting, multi-dimensional separations, and capillary connections to mass spectrometers. Such connectors can be used when the flow from a primary column exceeds the desired flow into a secondary column or when it is desirable to reduce the mass of sample entering the secondary column (analogous to using the split injection mode of sampling with a single column) or when it is desirable to provide a protective blanket gas when disconnecting capillary tubing from mass spectrometer interfaces. FIG. 11 illustrates a purged capillary tubing connector that comprises elements of the current invention. Purge gas is supplied to the union and acts not only to sweep column effluent from potentially stagnant spaces within the union but also provides the opportunity to monitor and potentially control pressure within the junction. This additional benefit can be useful when independent control of flow in the primary and secondary columns is desired.

Connections of capillary columns to purged unions suffer from some of the same usability and repeatability issues as those found with connecting capillary columns to inlets. In addition, insertion of column ends too far into the union can break the column ends, potentially leading to failed pneumatic seals or degraded performance. Not positioning columns in far enough creates peak tailing due to increased volume of the inter-column space and/or increased exposure of solutes to the sealing ferrule.

BRIEF SUMMARY OF THE INVENTION

Technical Problem

There are currently several potential problems that limit the usability, repeatability and performance of purged capillary column connections in gas chromatography. They include a wide variation in requirements specific for each type of gas chromatograph or purged device, the need for operators to have knowledge of these specific requirements for their devices, the skill of operators to install columns compliant with the requirements, and the stack up of variables that are outside of the operators' control when attaching capillary columns. In addition, current commercial versions of purged connectors and inlet liners contain compromises in their designs in order for them to be compatible with a wide range of capillary column dimensions.

Solution to the Problem

The embodiments of the invention comprise means to reduce or eliminate variability in column positioning, to provide features that prevent column seizing, to provide purged paths in tapered connectors that scale or track with the outer dimension of capillary columns inserted therein, and/or to simplify the process of connecting capillary columns to inlets or other purged capillary tubing connectors. The invention improves overall instrument performance and quality of analytical results by improving the reproducibility of sample transfer from the inlet to the capillary tubing connected thereto or between capillary tubes in the case of a purged connector. In addition, the current invention can improve laboratory productivity by simplifying the process of capillary tubing installation—a task that is performed daily in some analytical laboratories.

The arresting nature of the taper stops capillary tubing when it is inserted therein at a specific position where the narrowest radial axis of the taper equals the outer diameter of the capillary. This embodiment of the invention simplifies the process of capillary tubing installation and/or reduces variability in tubing positioning. When installing capillary tubing into a non-seizing purged taper, for example, one would first place the nut and ferrule on the tubing end and then trim a short section off the end. One would then simply insert the tubing into to the base of the inlet and within the taper in the base of the liner until it stops. Then one would tighten the nut to create a pneumatic seal. The requirement for instrument operators to measure and mark the tubing at a prescribed position is eliminated while the position of the column is reproducibly arrested in the correct position each time. By incorporating a non-seizing taper into purged capillary tubing connections, most of the variables associated with the current art are reduced or eliminated.

The arresting characteristic of the taper also provides a means of designing and producing purged connections for inlet liners or capillary tubing connectors that are optimal for a wide range of tubing dimensions. Whether optimal performance for a category of applications requires a constant open space for gas to flow around and by the column independent of column diameter or a space that scales with column diameter, the design of the taper shape and features can be adjusted to provide a very predictable column positioning and aspect ratio of tubing radial cross-sectional area to extra-tubing radial cross-sectional area. In this manner, a small number of taper designs will be applicable to a wide range of capillary tubing dimensions while still providing improved performance related to current commercial purged connections that have generic straight channel designs.

DETAILED DESCRIPTION OF THE INVENTION

Numerous specific details are set forth in the following exemplary embodiments to illustrate the principles of the invention. The embodiments are provided to illustrate aspects of the invention, but the invention is not limited to any embodiment. However, the invention may be practiced according to the claims without some or all of these specific details. For the purpose of clarity, technical material that is known in the technical fields related to the invention has not been described in detail so that the invention is not unnecessarily obscured. The scope of the invention encompasses numerous alternatives, modifications and equivalent; it is limited only by the claims.

The primary embodiment of the invention comprises a continuous taper into which columns are inserted until they stop and one or more flaws in the radial circularity of the taper that serves the dual purpose of preventing the column end from binding within the taper and providing a space for flow of gas past the end of the column.

FIGS. 8 through 11 comprise several exemplary implementations of the invention. In the preferred embodiment, the dimensions of the taper (feature 603 in FIG. 6) increases from a narrowest diameter of 0.2 mm at the top of the taper to 1.0 mm near the bottom in order to accommodate the range of typical capillary tubing outer diameters. The smallest diameter of the taper is small enough to prevent the smallest of the targeted capillary tubing from extending beyond the taper. The largest diameter is large enough to accept the largest outer diameter of the targeted capillary tubing. Other, wider or more limited ranges of taper diameters can be employed for reasons including but not limited to specific applications, manufacturing, commercial or performance objectives.

Figure 1:
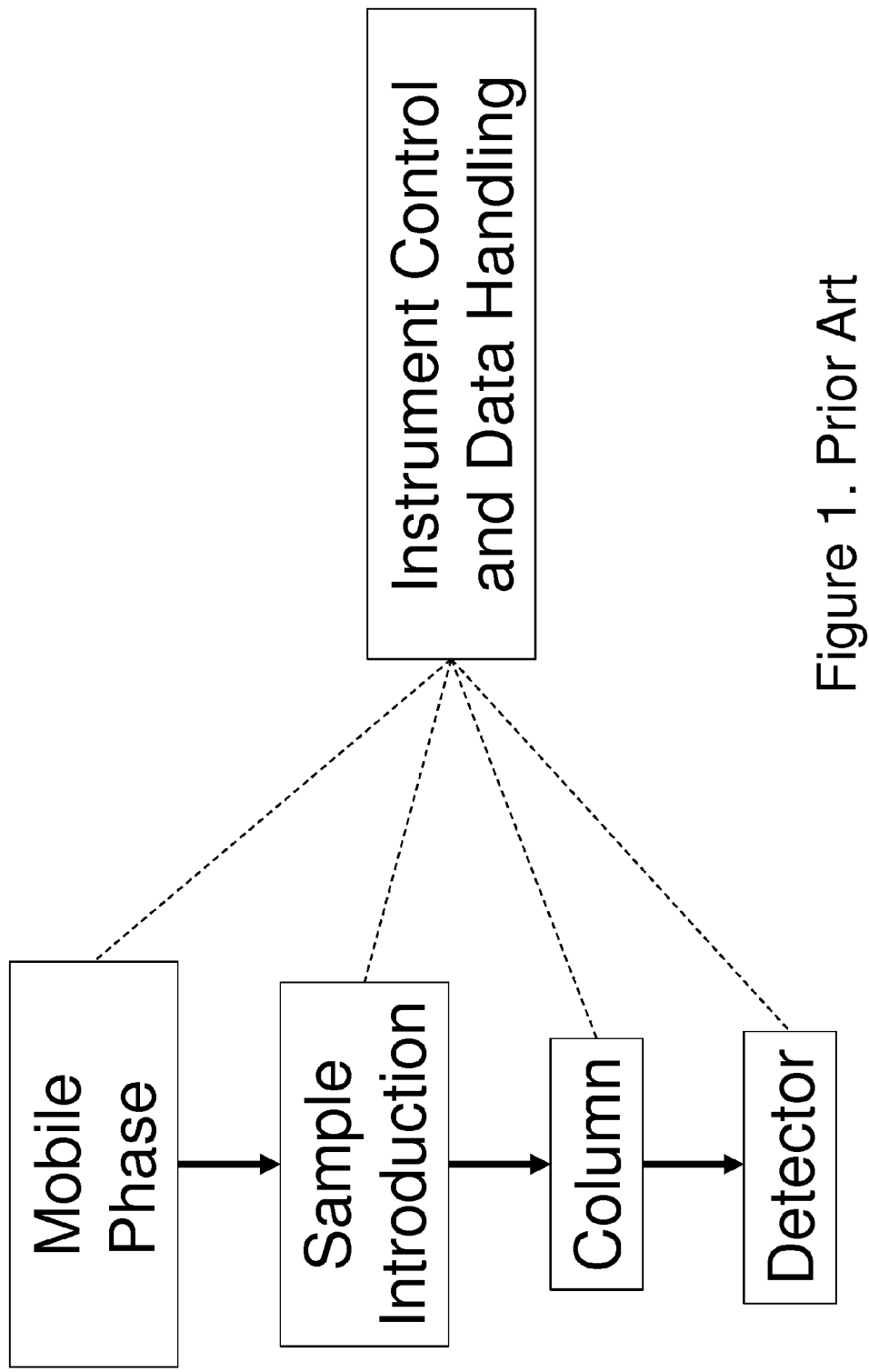
FIG. 1 is a block diagram of a general chromatographic instrument. A flowing mobile phase passes through a sample introduction stage and transfers sample to a chromatographic column. The flowing mobile phase continues to force transferred sample through the column wherein components can undergo partial or complete physical separation. As components exit from the column they are detected by a detector. Instrument control, data acquisition and processing are typically accomplished by a computerized controller.
Figure 2:
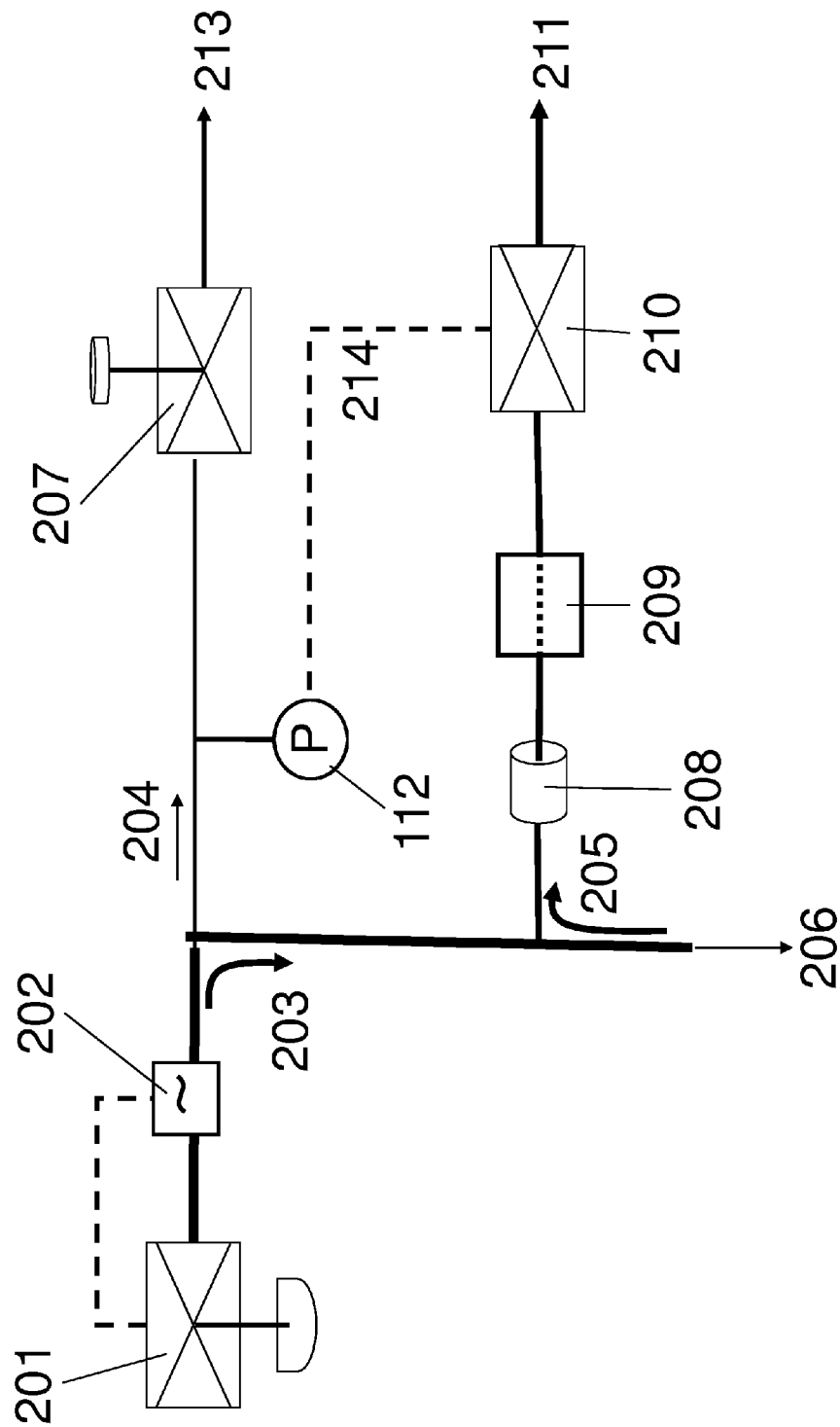
FIG. 2 illustrates a typical carrier gas flow diagram for a split/splitless inlet. A total mass flow of carrier gas is provided to the inlet through a feedback control loop comprising a proportioning valve 201 and a mass flow sensor 202. Upon entering the inlet, the total flow splits between septum purge flow 204 and flow 203 down the inlet liner. Flow control 207 controls septum purge flow as it flows to vent 213. Flow down the liner is subsequently split between column flow 206 and split vent/purge flow 205. Split vent/purge flow passes through a split vent trap 208, a split/purge ON/OFF solenoid 209, a proportioning valve 210, and then to waste 211. A pressure sensor 212 positioned on the septum purge line is used in a pressure control feedback loop with the proportioning valve 210 to effect backpressure control.
Figure 3:
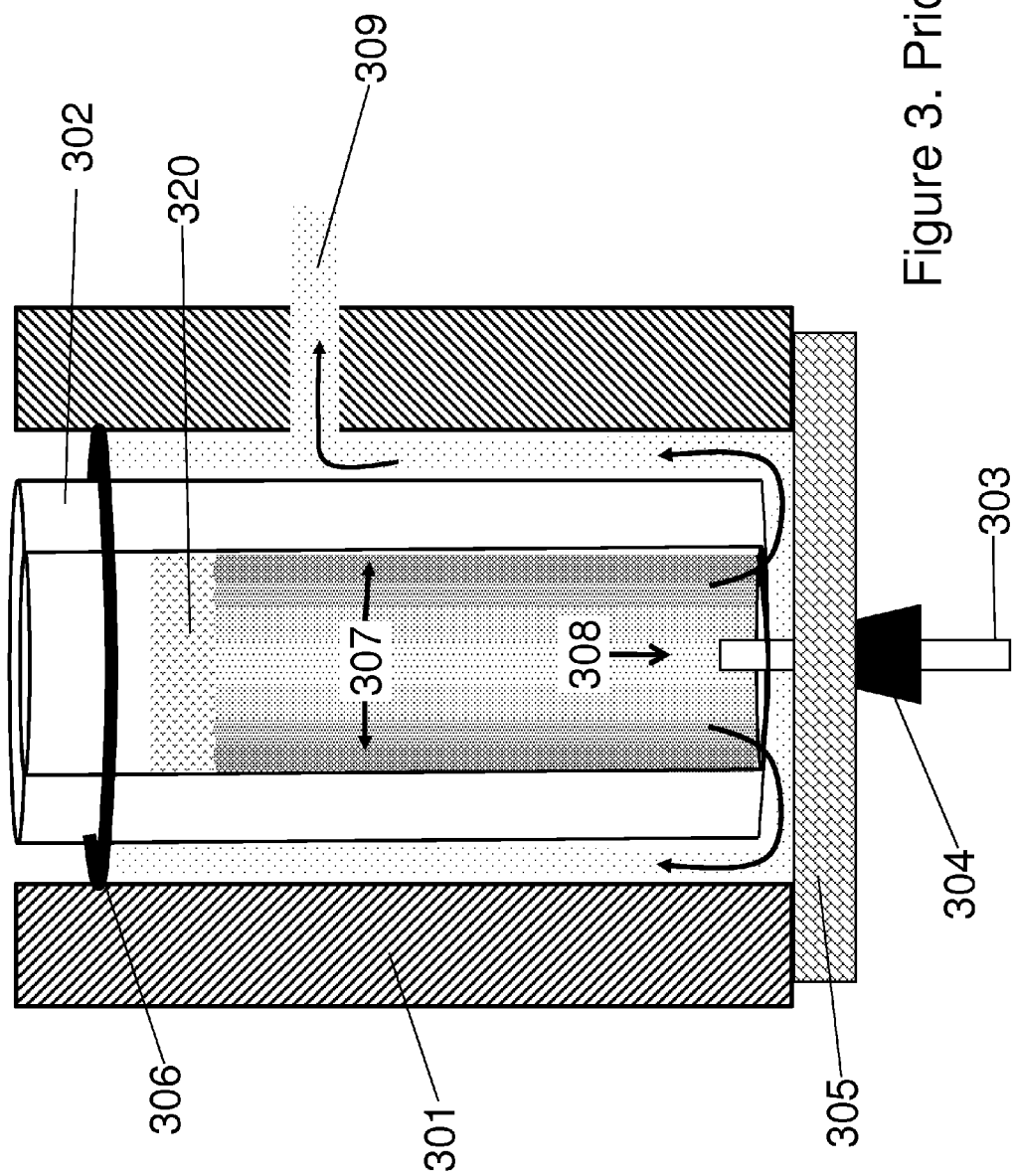
FIG. 3 illustrates a straight inlet liner typical of the current art which is known to increase sample discrimination against low-volatility solutes. The straight liner 302 is positioned within the inlet weldment 301, held in place and pneumatically sealed at the top of the inlet weldment by an O-ring liner seal 306. A capillary column 303 is sealed to the inlet baseplate 305 by a sealing ferrule 304. Upon liquid sample introduction onto a glass wool plug 310, the sample evaporates and a gradient 307 can form as sample vapors migrate down liner. The less volatile components have an affinity for the surface of the liner and spend proportionally more time near the inner liner wall than do lighter components, forming the analyte volatility gradient 307 across the liner. Non-representative sample vapors enter the head of the column 308. Split/purged sample vapors 309 travel to and vent out split vent.
Figure 4:
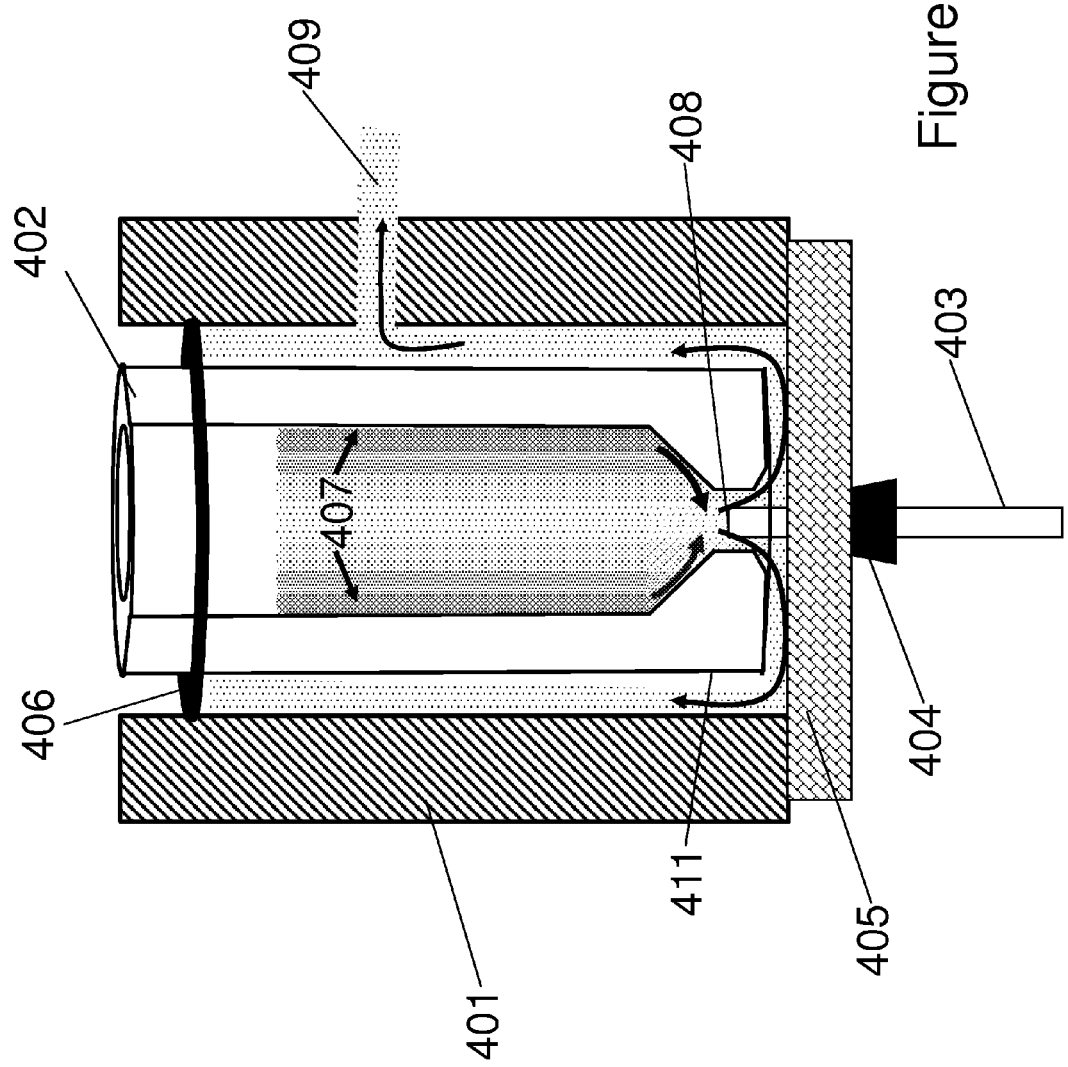
FIG. 4 illustrates the current art in liner design that includes a reduction in internal diameter at the liner base. A liner 402 has a straight channel of reduced inner diameter 411 at its base. The liner is positioned in inlet weldment 401 and is pneumatically sealed in place with O-ring seal 406. A capillary column 403 is sealed to the inlet baseplate 405 using a deformable ferrule 404 and is positioned within channel 411 at the liner base. A gradient 407 is formed as sample vapors migrate down liner; the less volatile components spending more time near the inner the liner wall. The liner wall is closer to the column entrance 408 as a result of the narrowing diameter at the liner base, so the less-volatile sample components near the liner wall are brought in closer proximity to the column entrance, thereby decreasing discrimination. Split/purge vapors 409 are vented out the split vent.
Figure 5:
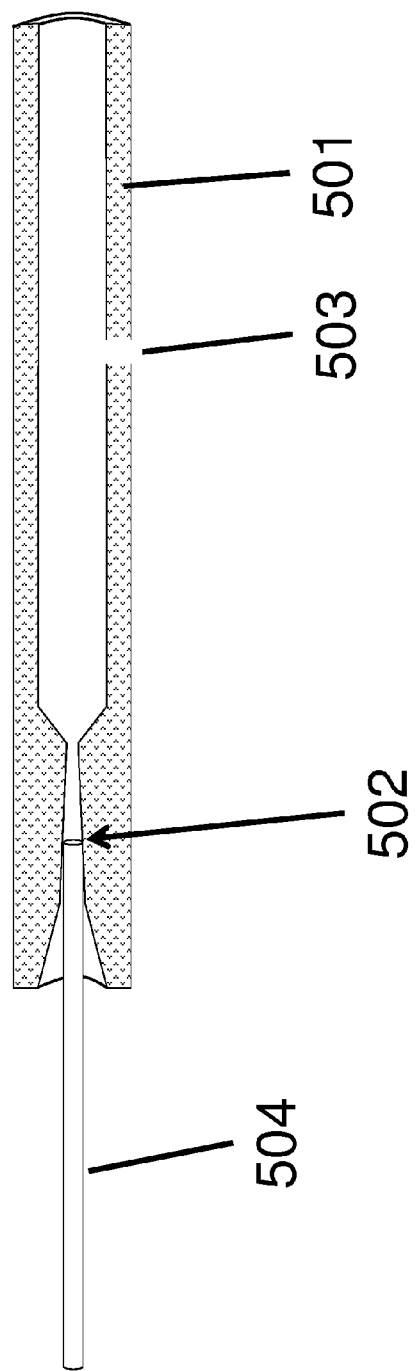
FIG. 5 illustrates a liner taper feature found in the current art splitless liner 501 designed to arrest and pneumatically seal the end of capillary tubing. Tubing seals in the taper 502 because the conical taper is radially symmetrical and the polyimide tubing coating is compressed between the underlying rigid fused silica tubing 504 and the surface of the taper during tubing installation. Since no flow can travel past the tubing sealed within the taper, a side port hole 503 must be used for purging and pneumatic control.
Figure 6:
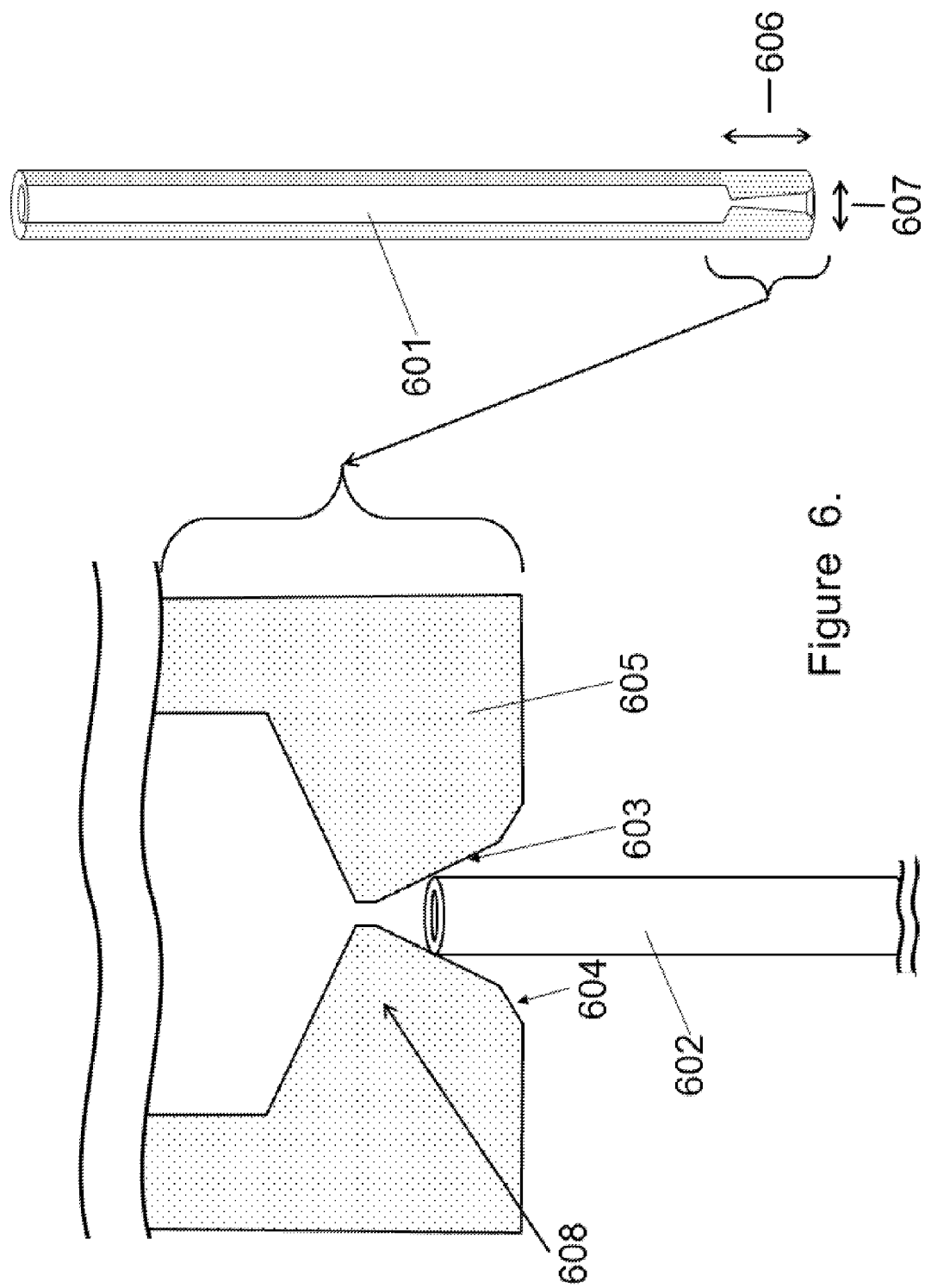
FIG. 6 illustrates an embodiment of the current invention integrated into the base of a gas chromatograph inlet liner 601. The exemplary taper stops capillary tubing at a predictable position 608 during installation while preventing formation of a pneumatic seal and while providing a path for gas to flow past the tubing. Capillary tubing 602 is inserted into an arresting taper 603 in the liner base until it stops. An optional additional taper 604 helps to initially guide the tubing into the arresting taper during installation. At least one radial axis 607 of the arresting taper decreases from a maximum near the base of the liner to a minimum as a function of position up the central axis 606 of the taper.

In an enhancement to the preferred embodiment, the base of liner leading to the arresting taper incorporates a secondary taper of a larger angle, as illustrated as feature 604 in FIG. 6. This feature helps guide tubing ends into the arresting taper. Use of alternate features can be employed in the liner bottom to facilitate guiding the tubing end into the arresting taper. All such features impact usability but have a much smaller impact on the most important performance and usability benefits associates with the arresting taper itself.

In the preferred embodiment, the arresting taper decreases linearly from its largest to smallest diameters. Linear tapers combine the benefits of being straightforward to manufacture reproducibly and to more reproducibly maintain the relationship of the extra-tubing radial cross-sectional open space at the point of to the tubing's cross-sectional area. Other shapes of arresting taper, such as concave or convex can alternately be employed to achieve specific goals such as those related to performance, usability, commerciality or manufacturability.

Figure 7:
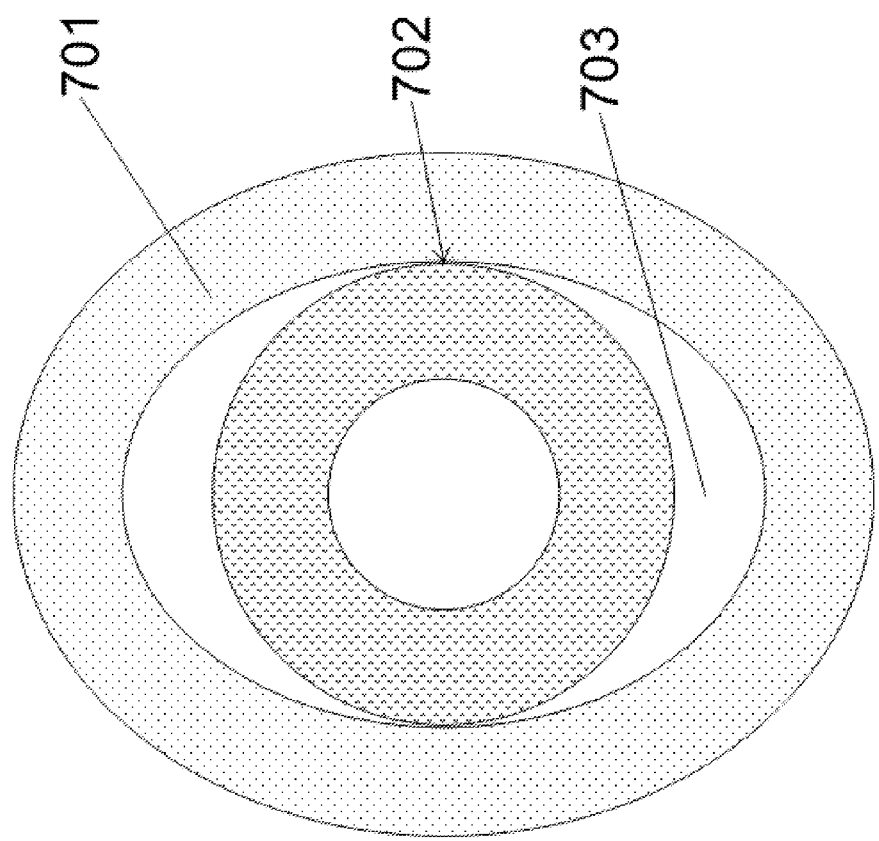
FIG. 7 illustrates the radial cross sectional view at the contact point of the end of capillary tube within a radially asymmetrical (in this case elliptical) taper 701. The end of capillary tubing stops within the taper during installation when the minor radial diameter of the noncircular taper matches the tubing's outer diameter 702. The taper's major radial diameter provides space 703 for gas flow past the tubing and provides a space for compressed tubing coating at the contact point with the taper to expand so that the tubing does bind to the surface of the taper.

The intended defects in circularity of the taper that prevent tubing seizing can take many forms depending on design and performance objectives. In the preferred embodiment, the defect comprises a distortion in the radial symmetry of the taper. FIG. 7 illustrates and example of this preferred embodiment in the form of an ellipse perpendicular to the central axis of the taper. By implementing a taper in the shape of an ellipse wherein both axes of the taper narrow with the same slope, a wide range of capillary tubing outer diameters can be accommodated with a single design while at the same time maintaining a constant ratio between the open space around the tubing end and the outer diameter of the tubing.

Alternate defects in the radial symmetry of the taper can be employed in order to meet specific performance, usability, commercial or manufacturability goals. Such alternative defects include but are not limited to incorporation of one more grooves in or ridges on the surface of the taper.

Figure 8:
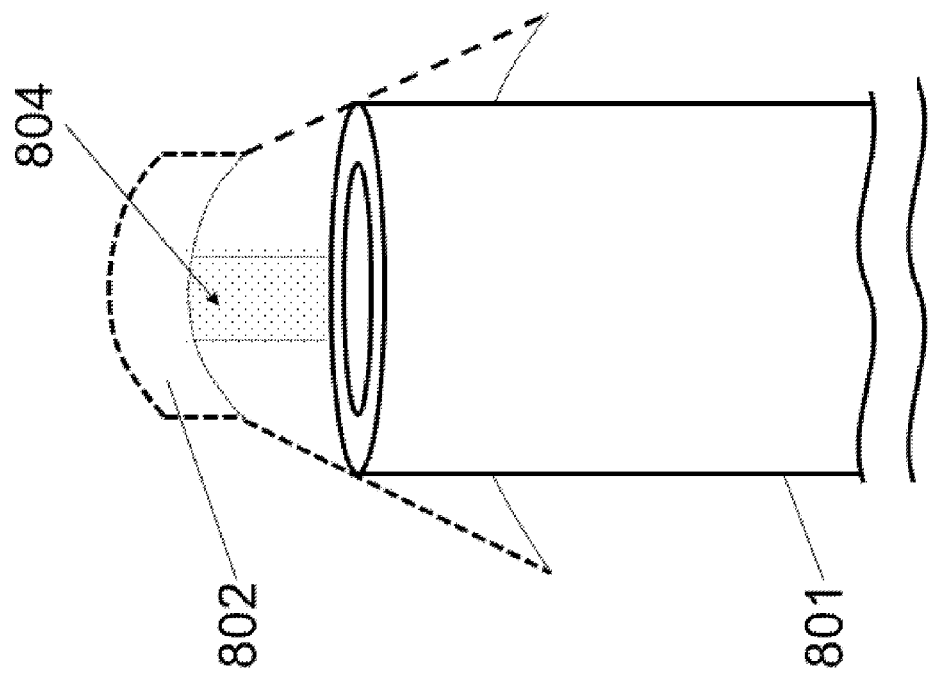
FIG. 8 illustrates a cut-away view 802 down the central axis of an exemplary taper at the bottom of a gas chromatograph liner comprising an exemplary groove defect as an alternative flaw in radial symmetry of the taper that prevents tubing seizing while providing a space for split/purge flow around the arrested tubing. Capillary tubing 801 is inserted until it stops in the conical taper 803. An exemplary groove 804 within inner surface of the taper runs the length of the taper
Figure 9:
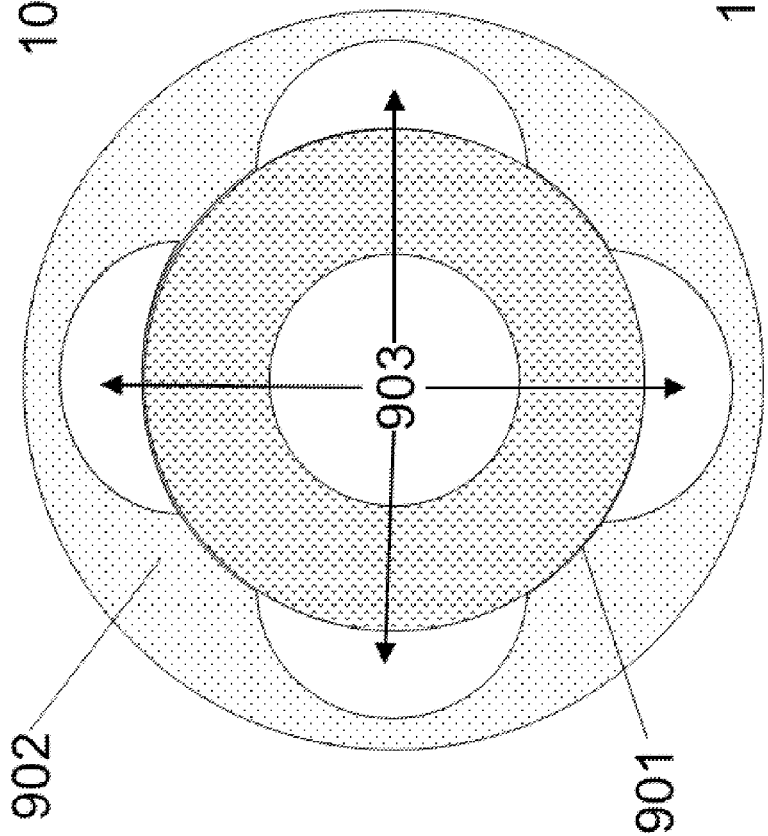
FIG. 9 illustrates the radial cross sectional view perpendicular to the central axis of an exemplary grooved taper 902 at the point of contact of the end of capillary tubing 901 arrested therein. In this example there are four similar grooves 903 evenly spaced on the inner surface of the taper. The grooves run down the length of the central axis of the taper and serve the dual purpose of preventing seizing of tubing to the taper and providing space for flow of purge gas around the tubing.

When grooves (troughs, indentations) of a constant shape and depth are maintained for the full length of the taper, they provide an extra-tubing space that is constant and independent of tubing diameter and arrested position within the taper, thereby providing relatively constant pneumatic resistance independent of tubing diameter. Exemplary groove defect features are illustrated in FIGS. 8 and 9.

Figure 10:
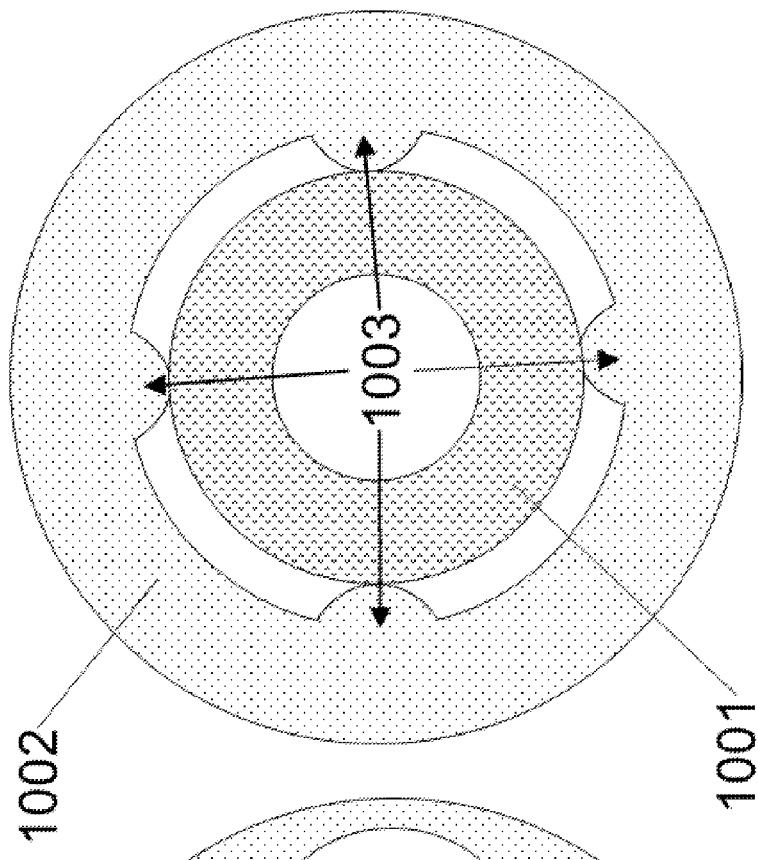
FIG. 10 illustrates the radial cross sectional view perpendicular to the central axis of an exemplary conical taper 1001 comprising ridges 1003 at the contact point of the end of a capillary tubing 1002 arrested therein. The ridges serve the dual purpose of preventing seizing of tubing to the taper and maintaining space for flow of gas around the tubing. In this example, there are four evenly spaced ridges of similar dimensions that run the length of the central axis of the taper.

The preferred embodiment of ridge defect comprises at least three ridges of equal dimensions that run the length of the arresting taper. The preferred ridges are rounded to minimize localized stress on the end the contacting tubing arrested within the taper to minimize the possibility of creating stress fractures or breakage. FIG. 10 illustrates a cross sectional view of an example of four such evenly spaced ridge defects. Alternate numbers of ridges, ridge shapes, or ridge positioning can be used in order to meet specific goals such as those relating to performance, usability, commerciality or manufacturability.

Figure 11:
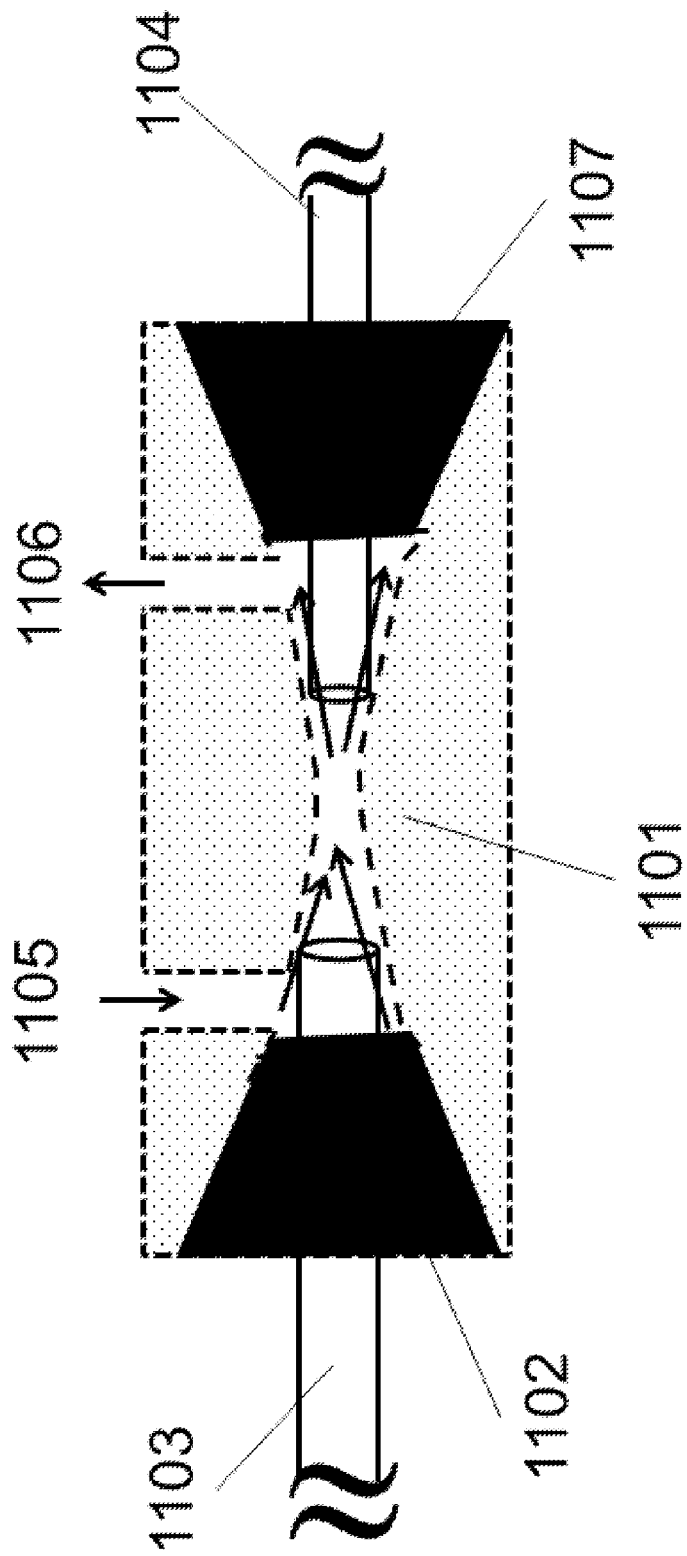
FIG. 11 illustrates a cross sectional view 1101 of an exemplary purged tubing connector comprising a non-seizing taper that allows gas flow around and/or past tubing ends. A primary tube 1103 is inserted into the union until it stops and then is pneumatically sealed to one side of the purged union using a ferrule 1102. Effluent from the primary tubing flows into the union. A purge gas 1105 flows into the union, around and past the primary tubing, sweeping primary tubing effluent through the union and by the entrance of a secondary tubing 1104 which has been inserted until it stops in an opposing taper and then pneumatically sealed using a ferrule 1107. In this example, any excess flow of gas that does not enter the secondary tubing is vented out port 1106.

In addition to use in gas chromatograph inlet liners, the embodiment of an arresting taper with flaws that prevent tubing seizing and provide space for flow of purge gas around the end of the tubing can be beneficial when used in other devices such as in purged tubing connectors. In addition to the other inherent benefits of the previously described embodiments, the ability to flow purge gas around and by the end of tubing provides the ability to sweep potentially stagnant voids within a tubing connector thereby minimizing peak tailing. The current invention also provides a means for venting excess flow such as might be required when the flow rate of gas from a first tube exceeds the desired flow rate into a second tube. An example of a purged tubing connector that employs an arresting taper with radial asymmetry is illustrated in FIG. 11.

The taper of the present invention can be formed from an inorganic crystalline material, such as fused silica, quartz, or glass. The process of forming the taper includes shaping the inorganic crystalline material through the use of a mandrel.

CONCLUSION

The disclosed embodiments are illustrative, not restrictive. While specific configurations of the non-seizing arresting tapers have been described, it is understood that the present invention can be applied to a wide variety of chromatographic devices that require connections of tubing. There are many alternative ways of implementing the invention.

The invention claimed is:

1. A continuously-narrowing taper incorporated into a purged connection for capillary gas chromatography that
 a. stops capillary tubing during installation at a predictable position within the taper and
 b. contains one or more features that prevent capillary tubing of a circular cross section from seizing within the taper and maintains an extra-tubular open space for gas to flow past the end of the capillary tubing.

2. The taper of claim 1 wherein the purged connection is a capillary gas chromatograph inlet liner.

3. The taper of claim 1 wherein the purged connection is a connector of two or more capillary tubes.

4. The taper of claim 1 wherein the diameter of at least one radial axis of the taper scales linearly relative to its position along the central axis of the taper.

5. The taper of claim 1 wherein the diameter of at least one radial axis of the taper scales non-linearly relative to its position along the central axis of the taper.

6. The taper of claim 1 wherein the radial cross-sectional area of the extra-tubular open space at the contact position of a capillary tube of circular cross section arrested within the taper is constant and independent of tubing diameter and arresting position along the central axis of the taper.

7. The taper claim 1 wherein the radial cross-sectional area of the extra-tubular open space at the arrested position of the capillary tube of circular cross section within the taper scales as a function of tubing diameter and arresting position along the central axis of the taper.

8. The taper of claim 1 wherein the feature in the taper that prevents seizing and maintains space for extra-tubular gas flow comprises one or more grooves in the surface of the taper.

9. A capillary gas chromatograph inlet liner comprising the taper of claim 8.

10. The taper of claim 1 wherein the feature in the taper that prevents seizing and provides space for extra-tubing flow comprises one or more ridges on the surface of the taper.

11. The taper of claim 10 comprised in a capillary gas chromatograph inlet liner.

12. The taper of claim 1 wherein the feature of the taper that prevents seizing and maintains space for extra-tubular gas flow comprises a radial asymmetry perpendicular to the central axis of the taper.

13. The taper of claim 12 wherein the form of the radial asymmetry is elliptical.

14. The taper of claim 13 comprised in a capillary gas chromatograph inlet liner.

15. The process of forming the taper of claim 1, comprising:
 a. providing an inorganic crystalline material, and
 b. using a mandrel to shape the inorganic crystalline material to form the taper.

* * * * *